United States Patent [19]

Overman et al.

[11] Patent Number: 4,675,325

[45] Date of Patent: Jun. 23, 1987

[54] SYNTHESIS OF INDOLIZIDINES RELATED TO THE CARDITONIC PUMILIOTOXIN A ALKALOIDS

[75] Inventors: Larry E. Overman, Corona Del Mar, Calif.; Fumitaka Ito, Sendai, Japan

[73] Assignee: The Regents of the University of California, Berkeley, Calif.

[21] Appl. No.: 622,790

[22] Filed: Jun. 21, 1984

[51] Int. Cl.⁴ .................. A61K 31/475; C07D 221/02
[52] U.S. Cl. ..................................... 514/299; 546/183
[58] Field of Search ........................ 546/183; 514/299

[56] References Cited

PUBLICATIONS

Overman, Grant Application HL2585404, issued Jun. 14, 1983.
Overman et al., Tetrahedron Letter, 1982, 23, pp. 2355-2358.
Mensah-Dwumah et al., Toxicon, 1978, 16, 189.
Mensah-Dwumah et al., Chem. Abst. 89-101361 M(1978), eq. Toxicon, 1978, 16, 189.
Overman et al., J. Am. Chem. Soc. 1981, 103, 1851-1853.
Torregrosa et al., Tetrahedron, vol. 38, No. 15, pp. 2355-2363 (1982).
Albuquerque et al., Chem. Abst. 98:49103y.
Uemura et al., Chem. Abst. 98:89705c.
Overman et al., Chem. Abst. 95:25362u.
Daly et al., Chem. Abst. 90:81807b.
Tamburini et al., Chem. Abst. 95:198684d.
Daly et al., Chem. Abst. 92:215600f.
Overman et al., American Chemical Society, Washington D.C., 1980, Abstract paper, ORGN 25.
Tamburini, R. et al., "Inhibition of Calcium-Dependent ATPase from Sarcoplasmic Reticulum by a New Class of Indolizidine Alkaloids, Pumiliotoxins A, B, and 251D", Journal of Neurochemistry, (1981) 37(3):775-780.
Witkop, B., and E. Gossinger, The Alkaloids, (24:200), Eds. Arnold & Brossi.

Primary Examiner—Donald G. Daus
Assistant Examiner—Cecilia Shen
Attorney, Agent, or Firm—Brown, Martin, Haller & Meador

[57] ABSTRACT

A method of making dendrobatid alkaloids with the formula

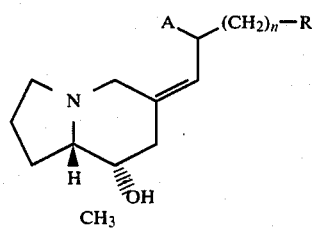

in which A is either $CH_3$ or H, and n is an integer from 1-9, and R is $CH_2OH$, CHO,

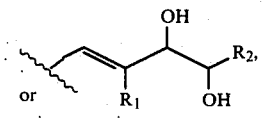

and $R_1$ and $R_2$ are alkyl groups; and the use of such alkaloids to treat cardiovascular illness.

18 Claims, 4 Drawing Figures

SYNTHESIS OF INDOLIZIDINES RELATED TO THE CARDITONIC PUMILIOTOXIN A ALKALOIDS

This invention was made with government support under Grant No. HL25854 awarded by the National Institute of Health. The government has certain rights in this invention.

FIELD OF INVENTION

This invention relates to indolizidine chemical intermediates, methods of preparing the same, and uses of the intermediates to prepare dendrobatid alkaloids.

BACKGROUND OF THE INVENTION

The skin of the Central American poison frogs, *Dendrobates pumilio*, contains a variety of alkaloids, some of which are known cardioactive agents as described by Witkop in The Alkaloids, Page 200, Volume 24 (Eds. Arnold and Brossi). Unfortunately, however, these chemicals have not been employed for medical treatment because they are not practically obtainable from natural sources. One group, consisting of two structural distinct subgroups, termed pumiliotoxins A and B was discovered as early as 1967 and with their allo equivalents includes at least 24 members. While structural studies have shown that these toxins share the unusual (Z)-6-alkylideneindolizidine ring system which carries side chains at positions C-6 and C-8 with the C-6 chain being connected to the ring by an exocyclic double bond, there have been no reports detailing methods whereby pumiliotoxins A or B can be made, and only one describing the synthesis of a simple pumiliotoxin A alkaloid 251D. Pharmacological studies have shown that pumiliotoxin B is a considerably more potent cardioactive drug than pumiliotoxin 251D. Thus, a method which would permit the practical synthesis of pumiliotoxin B and related dendrobatid alkaloids would facilitate their use in the treatment of cardiovascular disorders.

Although there hve been no previous reports on the synthesis of pumiliotoxin B, two related but structurally distinct pumiliotoxin A alkaloids, specifically pumiliotoxins 251D and 237A have recently been synthesized. Neither the synthesis of pumiliotoxins 237A nor 251D, however, involve the use of the key indolizidine alcohol and aldehyde intermediates which is the subject matter of the present invention. Moreover, neither synthesis employs the use of the ylide used in the present invention to generate pumilitoxin B.

As stated previously, there is at present no known synthetic scheme whereby pumiliotoxins B can be generated. However, a recent report by the present inventor has described a method that is useful for the stereo controlled synthesis of the side chain connected to the (Z)-6-alkylideneindolizidine ring system, that is, a method for assembling the allyic diol functionality of pumiliotoxin B. This work was done on model chemicals that do not contain an indolizidine ring, specifically (2S,4E)-heptenones, and these chemicals have no known cardioactive property.

SUMMARY OF THE INVENTION

According to the present indolizidine invention, alcohol and aldehyde intermediates are synthesized wherein the intermediates are generated from a reaction of trialkylsilyl-ω-primary ethers with oxiranes, and subsequent reaction steps. The key indolizidine aldehyde intermediates upon subsequent reaction with suitable ylides yield pumiliotoxin B dendrobatid alkaloids.

DETAILED DESCRIPTION OF INVENTION

Figure 1:
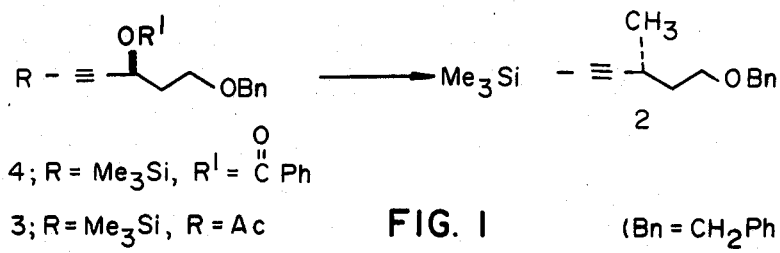
FIG. 1 shows silylalkyne, 2, used in the synthesis of indolizidine intermediates.
Figure 2:
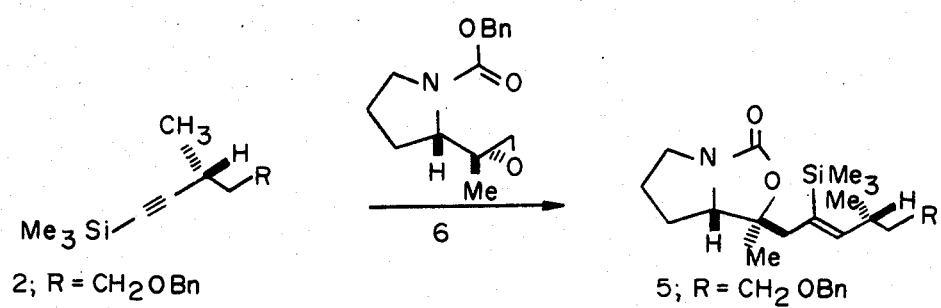
FIG. 2 depicts the synthetic scheme for the indolizidine alcohol and aldehyde intermediates.
Figure 2:
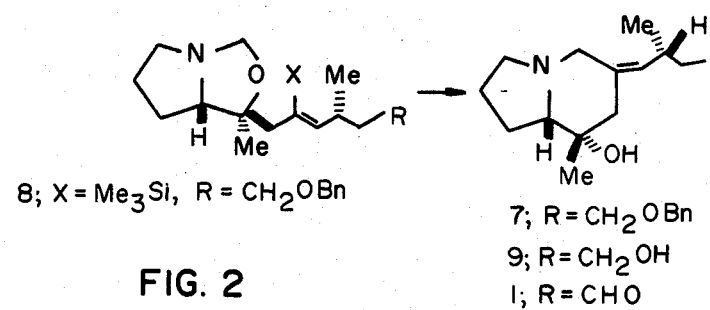

The invention described herein relates to chemical intermediates that are useful to synthesize cardioactive drugs. Accordingly, we have produced novel alcohol and aldehyde indolizidine intermediates that are practically useful in the synthesis of dendrobatid alkaloids. The novel aldehyde intermediate is generated from the alcohol intermediate and the former is reacted with a novel ylide to make dendrobatid alkaloids.

(A) Synthesis of the key alcohol and aldehyde indolizidine intermediates

To generate indolizidine alcohol and aldehyde intermediates useful in the synthesis of pumiliotoxin B, it is necessary to assemble a chiral silylalkyne from esters of (S)-5-(benzyloxy)-1-trimethyl-silyl-1-pentyn-3-ol. This involves the reduction of 3-(benzyloxy)propanitrile, the latter reagent being prepared from acrylonitrile and benzyl alcohol as described by Gaiffe and Launay in Academy of Science, Serial C, Pages 1379–1380 (1968), with i-Bu$_2$AlH to give 3-benzyloxy propanal which is condensed with ethynyllithium, prepared as described by Midland in the Journal of Organic Chemistry, Volume 40, Page 2250 (1975), to yield the racemic propargylic alcohol in about 50% yield following distillation. Reaction of the propargylic alcohol with R-(+)-2-methylbenzylamine gives the corresponding diastereomeric carbamates that upon chromatographic separation and carbamate cleavage with Cl$_3$SiH as described by Pirkle in the Journal of Organic Chemistry, Volume 42, Page 2781 (1971) yields the (S)-alcohol and (R)-alcohol derivatives in yields of about 20%.

Isolation of the (S)-alcohol and subsequent carbon silylation and acetylation yields the (S)-acetate in about 50% yield. The corresponding (S)-benzoate can be prepared from the (R)-alcohol similarly by carbon silylation followed by Mitsunobu inversion with benzoic acid. Either the (S)-acetate or the (S)-benzoate upon reaction with the Me$_2$CuMgBr in THF gives the sought after silylalkyne in about 50% yields from either reagent.

Next, silylalkyne is sequentially reacted at 22° C. with i-Bu$_2$AlH and MeLi, followed by reaction with the appropriate chiral epoxide generated from L-proline as described by Overman in the Journal of the American Chemical Society, Volume 103, Pages 1851 (1981) to yield the corresponding bicyclic carbamate. Base hydrolysis of the latter at 90° C. followed by reaction of the amino alcohol at room temperature with aqueous formalin yields a cyclopentaoxazolidine which is cyclized to the desired Z-alkylideneindolizidine by reaction with camphorsulfonic acid in refluxing acetonitrile. Chromatographic purification gives the Z-alkylideneindolizidine in about 50% yield. Debenzylation of the Z-alkylideneindolizidine by conventional methods yields the key alcohol intermediate which upon subsequent oxidation with the Swern reagent by the general procedure described by Swern in the Journal of Organic Chemistry, Volume 43, Page 2480 (1978) provides the important indolizidine aldehyde intermediate.

(B) Synthesis of Ylide:

In order to obtain the proper stereochemistry of the side chain allylic diol of pumiliotoxins B, it is necessary to prepare a ylide with suitable stereochemistry. This is accomplished by inversion of ethyl L-lactate by the general procedure of Mitsunobu described in Synthesis, Volume 1, Page 1 (1981) at $-20_0$ C.° in THF to give the corresponding (R)-p-nitrobenzoyl ester. The latter reagent is deacylated with $K_2CO_3$ in anhydrous ethanol and the alcohol produced protected using the general technique of Hanessian and Lavallee described in the Canadian Journal of Chemistry, Volume 55, Page 562 (1978) as the t-butyldiphenylsilyl ether. Finally, ylide is generated by way of the 2-pyridinethiol ester as described by Overman and McCreedy in Tetrahedron, Volume 23, Page 2355 (1982).

(C) Reaction of indolizidine aldehyde with ylide:

To generate pumiliotoxin B reaction of indolizidine aldehyde intermediate with ylide is effected by refluxing in $CH_2Cl_2$ to yield the corresponding enone that upon threo selective reduction with $LiAlH_4$ and accompanying desilylation gives pumiliotoxin B. Subsequent chromatographic purification yields, in about 95% isomerically pure form, pumiliotoxin B.

EXAMPLE I

Preparation of (8S,8aS)-8-Hydroxy-8-methyl-6Z-[4-oxo-2R-methylbutylidene]octahydroindolizidine (1)

In order to make the key intermediate (8S,8aS)-8-Hydroxy-8-Methyl-6Z-[4-oxo-2R-methylbutylidene]octrahydroindolizidine (1) the following reactions are carried out as diagramed in FIGS. 1 and 2. The numbers that refer to reagents in the text below correspond to reagents in the diagram.

(a)

(R)-5-(Benzyloxy)-3-Methyl-1-(trimethylsilyl)pentyne (2) (FIG. 1)

Using the general procedure of McDonald, described in the Journal of Organic Chemistry, Volume 45, Page 4740 (1980), a solution of the (S)-acetate 3 (4.50 g, 14.8 mmol) and THF (15 mL) was added at 23° C. dropwise to the cuprate reagent prepared in THF (75 mL) from CuI (2.81 g, 29.6 mmol) and MeMgBr (31 mL) of a 1.9M solution in ether). After 10 min at 23° C., the reaction was quenched by adding it dropwise to an excess of $NH_4Cl$ (saturated aq). Isolation (ether, $MgSO_4$) and chromatographic purification (20:1 hexane ethyl acetate) gave 1.98 g (51%) of 2 as colorless liquid: 98.7% pure by GLC analysis; $[a]_D^{25}-64.0$ (c 2.26, $CHCl_3$); IR (film) 2167, 1262, 1100 $cm^{-1}$; $^1H$ NMR (250 MHz, $CDCl_3$) 7.2–7.4 (m, Ph), 4.52 (s, $OC\underline{H_2}Ph$), 3.61 (apparent t, J=6.5 Hz, $CH_2C\underline{H_2}O$), 2.6–2.75 (m, $C{\equiv}C\underline{C}H$), 1.65–1.80 (m), 1.18 (d, J=7.0 Hz, Me), 0.13 (s, $Me_3Si$); MS (isobutane CI) m/z 261 (MH), 233, 187, 171, 129, 103, 91, 79, 73; MS (EI) m/z 245.1368 (245.1362 calcd for $C_{15}H_{21}OSi$, M-Me).

An identical procedure can also be used to prepare 2 from benzoate 4 (3.98 g, 10.8 mmol): yield 1.23 g (44%); $[a]_D^{25}-64.4$ (c 1.42, $CHCl_3$).

(b)

Synthesis of (1S,7aS)-Tetrahydro-1-methyl-1-[6-(benzyloxy)-4R-methyl-2-(trimethylsilyl)-2Z-hexenyl]-1H,3H-pyrrolo[1,2-c]oxazol-3-one (5) (FIG. 2)

Neat i-$Bu_2AlH$ (0.85 mL, 4.8 mmol) was added dropwise at 23° C. to a solution of 2 (1.23 g, 4.74 mmol) and hexane (3 mL). After 0.5 h THF (8 mL) was added followed by the dropwise addition of MeLi (2.6 mL of a 1.33M solution in ether, 3.5 mmol). The color changed from colorless to light pink when the last drop of MeLi was added, and slowly changed over 0.5 h to light yellow as this solution was maintained at 23° C. A solution of epoxide 6 (520 mg, 1.99 mmol made as described by Overman in the Journal of the American Chemical Society, Volume 103, Page 1851 (1981) and THF (2 mL) was then added and the resulting solution was heated at 60° C. for 25 h. Workup gave a yellow oil which was purified by chromatography (4:1 hexane-ethyl acetate) to give 637 mg (77% based on 12) of 5 as a colorless oil: $[a]_D^{25}-39.2$ (c 1.05, $CHCl_3$); IR (film) 1760 $cm^{-1}$; $^1H$ NMR (250 MHz, $CDCl_3$) 7.2–7.4 (m, Ph), 5.87 (d, J=10.6 Hz, =CH), 4.48 (AB quartet, J=11.9 Hz, $OC\underline{H_2}Ph$), 3.53–3.66 (m, NCH and $NC\underline{H}H$), 3.46 (apparent t, J=6.8 Hz, $CH_2O$), 3.05–3.2 (m, $\underline{N}CHH$), 2.55–2.65 (m, $=CHC\underline{H}$), 2.56 (AB quartet, J=13.7 Hz, $CH_2C=$), 1.5–2.2 (m), 1.30 (s, C-8 Me), 0.99 (d, J=6.6 Hz, $CH\underline{Me}$), 0.17 (s, $Me_3Si$); MS (isobutane CI m/z 416 (MH), 372, 186, 139, 107, 91, 70; MS (EI) 400.2306 (400.2307 calcd for $C_{23}H_{34}NO_3Si$, M-Me).

(c)

(8S,8aS)-8-Hydroxy-8-methyl-6Z-[4-(benzyloxy)-2R-methylbutylidene]octahydroindolizidine (7) (FIG. 2)

A carefully degassed solution of 5 (527 mg. 1.27 mmol), KOH (1.8 g, 25 mmol), EtOH (1.6 mL) and $H_2O$ (0.4 mL) was heated at 90° C. for 12 h. After cooling to 23° C., 37% aq formalin (1 mL) and MeOH (2 mL) were added dropwise. After 4 h the reaction was concentrated and the crude oxazolidine 8 (496 mg) was isolated ($CH_2Cl_2$, $K_2CO_3$): MS (isobutane CI m/z 402 (MH).

A mixture of this oxazolidine sample, paraformaldehyde (180 mg, 6.0 mmol), camphorsulfonic acid (650 mg, 2.8 mmol), and acetonitrile (10 mL) was heated at 80° C. for 13 h. Isolation (ether, $K_2CO_3$) gave a brown oil which was purified by radial chromatography (silica gel, 50:1:0.1 $CHCl_3$-MeOH-12N $NH_4OH$) to afford 219 mg (52%) of 7 as a light yellow oil: pure by TLC analysis; $[a]_D^{23}-25.5$ (c 2.33, $CHCl_3$); IR (film) 3200-3600, 1100 $cm^{-1}$; $^1H$ NMR (250 MHz, $CDCl_3$) 7.2–7.4 (m, Ph), 5.02 (br d, J=9.7 Hz, =CH), 4.45 (apparent s, $OCH_2Ph$), 3.82 (d, J=11.8 Hz, H-5α), 2.29 (br d, J=11.8 Hz, H-5β), 1.13 (s, C-8 Me), 1.00 (d, J=6.6 Hz, C-11 Me); MS (isobutane CI) m/z 330, 166, 107, 91, 83, 70; MS (EI) m/z 329.2338 (329.2355 calcd for $C_{21}H_{31}NO_2$).

(d)

(8S,8aS)-8-Hydroxy-8-methyl-6Z-[4-hydroxy-2R-methylbutylidene]octahydroindolizidine (9) (FIG. 2)

A solution of 7 (164 mg., 0.500 mmol), THF (8 mL) and $NH_3$ (8 mL) was treated with excess Li until the blue color persisted for 3 h. Addition of excess $NH_4Cl$ was followed by evaporation of the $NH_3$ and isolation with $CHCl_3$ ($K_2CO_3$) to give, after radial chromatography (silica gel, 20:1:0.1 CHCl$_3$-MeOH-12N NH$_4$OH), 73.1 mg (61%) of 9 as a colorless oil: isomerically pure by TLC analysis (R$_f$ 0.4, C-11 epimer R$_f$ 0.5; 10:1.0:0.1 CHCl$_3$-MeOH-12N NH$_4$OH), [a]$_D^{25}$ −22.1 (c 1.87, CHCl$_3$); IR (film) 3100–3600, 1670 cm$^{-1}$; $^1$H NMR (250 MHz, CDCl$_3$) 5.06 (br d, J=9.8 Hz, =CH), 3.82 (d, J=11.8 Hz, H-5α), 3.45–3.65 (m, CH$_2$O), 3.0–3.12 (m, NCHH), 2.7 (br s, OH), 2.55–2.70 (m, =CCH), 2.37 (br d, J=11.9 Hz, H-5β), 2.17–2.3 (m, NCHH), 2.14 (ABq, J=14.0 Hz, CH$_2$C=), 1.5–2.3 (m), 1.14 (s, C-8 Me), 1.02 (d, J=6.6 Hz, C-11 Me); MS (EI) m/z 239.2876 (239.1885 calcd for C$_{14}$H$_{25}$NO$_2$).

This key alcohol indolizidine intermediate could be stored in a freezer under Ar for several months with only slight decomposition.

(e)

(8S,8aS)-8-Hydroxy-8-methyl-6Z-[4-oxo-2R-methyl-butylidene]octahydroindolixidine (1)

Lastly, the formation of the key aldehyde intermediate 1 was made from alcohol 9 (240 mg, 1.00 mmol) by oxidation with oxalyl chloride (3 mmol) and Me$_2$SO (6 mmol) using the general procedure developed by Swern as described in the Journal of Organic Chemistry, Volume 43, page 2480 (1978), to give, after radial chromatography (silica gel, 25:1:0.1 CHCl$_3$-MeOh-12N NH$_4$OH), 211 mg (88%) of 1 as a slightly impure pale yellow oil: [a]$_D^{25}$ −25.9 (c 0.63, CHCl$_3$); IR (film) 3100–3700, 1718, 1030 cm$^{-1}$; $^1$H NMR (250 MHz, CDCl$_3$) 9.67 (t, J=2.0 Hz, CHO); MS (isobutane CI) m/z 238 (MH), 117, 99. 1 should be used immediately in the olefination step in the preparation of pumiliotoxins B.

EXAMPLE II

Preparation of Pumiliotoxin B using indolizidine aldehyde intermediates

The intermediate (8S,8aS)-8-hydroxy-8-methyl-6Z-[4-oxo-2R-methylbutylidene]octhydroindolizidine (1) can be used to produce pumiliotoxin B (12) by carrying out the following set of seguential reactions:

(a)

Figure 4:
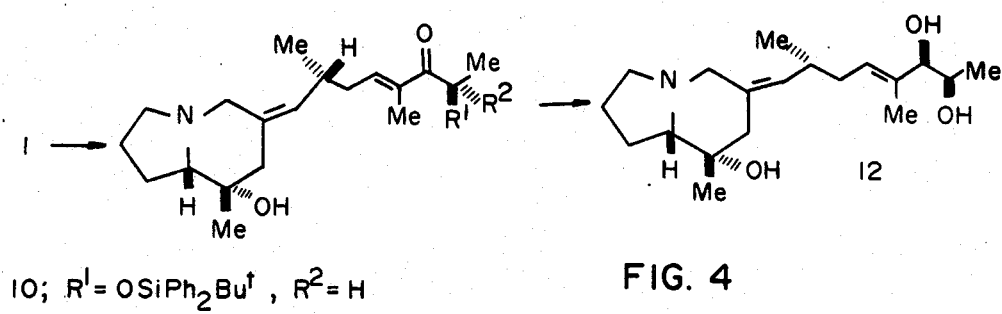
FIG. 4 depicts the preparation of pumiliotoxins B.

Formation of (8S,8aS)-8-Hydroxy-8-methyl-6-Z[6-oxo-2R,5-dimethyl-7R-(t-butyldiphenylsilyoxy)-4E-octenylidene]octahydroindolizidine (10) (FIG. 4)

A carefully degassed solution of 1 (53.3 mg, 0.224 mmol), ylide 11 (194 mg, 0.323 mmol), and CH$_2$Cl$_2$ (1 mL) was heated at reflux for 5 d. Concentration and purification of the residue by radial chromatography (silica gel, 40:1:0.1 CHCl$_3$-MeOH-NH$_4$Oh) gave 136 mg of a light yellow oil which was a ~2:1 mixture of 10 and Ph$_3$PO. This mixture was difficult to separate and it was typically used directly in the reduction step, since Ph$_3$PO and 12 are easy to separate by chromatography.

A 30 mg portion of this crude oil was purified by careful preparative TLC (R$_f$ 0.3, 40:1 CHCl$_3$-MeOH, eluted twice), to give 19.3 mg (71%) of chromatographically homogeneous 10 as a colorless oil: [a]$_D^{25}$ +13.2 (c 0.87, MeOH); IR (film) 3100–3600, 1685, 1110 cm$^{-1}$; $^1$H NMR (250 MHz, CDCl$_3$) 7.2–7.7 (m, Ph), 6.19 (br t, J=7.3 Hz, CH=CCO), 5.01 (br d, J=9.8 Hz, =CH), 4.69 (q, J=6.8 Hz, CHOR), 3.74 (d, J=11.7 Hz, H-5α), 3.2–3.1 (m), 2.5–1.6 (m), 1.54 (br s, =CMe), 1.24 (d, J=6.8 Hz, ROCHMe), 1.08 (s, C-8 Me), 1.00 (s, t-Bu), 0.89 (d, J=6.5 Hz, CHMe); MS (isobutane CI) m/z 560 (MH), 304, 279, 257, 231; MS (EI) m/z 559.3463 (559.3480 calcd for C$_{35}$H$_{49}$NO$_3$Si).

(b)

Formation of (+)-Pumiliotoxin B (12) (FIG. 4)

A solution of pure enone 10 (14.6. mg, 0.026 mmol) and THF (0.5 mL) was added dropwise at −20° C. to a rapidly stirred suspension of LiAlH$_4$ (8 mg, 0.2 mmol) and THF (1.5 mL). After 0.5 h, the cooling bath was removed and the mixture was allowed to warm to 23° C. After 2 h, Na$_2$SO$_4$.10H$_2$O (0.1 g) was added followed by CHCl$_3$ (5 mL), and the resulting mixture was stirred rapidly for 2 h and then filtered through Celite. The concentrated filtrate was purified by radial chromatography (silica gel, 10:1:0.1 CHCl$_3$-MeOH-12N NH$_4$OH) to give 6.2 mg (74%) of 12 as a colorless oil. This sample was chromatographically homogeneous, but contained 6% of the erythro diastereomer ($^1$H NMR analysis of the p-bromophenylboronides). An analytical specimen of synthetic 12 was obtained from the center cut of a chromatographic purification of a larger sample of comparable material: [a]$_D^{25}$+19.3, [a]$_{578}^{25}$+19.7, [a]$_{546}^{25}$+23.0, [a]$_{435}^{25}$+40.2 (c 1.00, MeOH); IR (film) 3100–3600, 1455, 1375, 1310, 1090, 1028, 966 cm$^{-1}$; $^1$H NMR (250 MHz, CDCl$_3$, 4.7 mg/0.5 mL) 5.39 (br t, J=6.7 Hz, H-13), 5.06 (br d, J=9.6 Hz, H-10), 3.7–3.9 (m, H$_{5α}$ and H-16), 3.70 (apparent d, J=7.1 Hz, H-15), 3.0–3.1 (m, H-3α) 2.66 (br s, OH), 2.42–2.57 (m, H-11), 2.34 (br d, J=11.7 Hz, H-5β), 1.65–2.32 (m), 1.58 (br s, H-19, 1.13 (s, H-9), 1.11 (d, J=6.0 Hz, H-17), 1.00 (d, J=6.6 Hz, H-18); $^{13}$C NMR (63 MHz, CDCl$_3$) 135.4, 133.9, 130.7, 127.6, 82.9, 71.8, 69.0, 68.6, 54.7, 53.4, 49.0, 35.7, 32.6, 24.5, 23.4, 21.5, 21.3, 19.1, 12.4, MS (EI) m/z 323.2466 (323.2460 calcd for C$_{19}$H$_{33}$NO$_3$ 18%), 306 (10%), 278 (40%), 206 (23%), 194 (53%), 193 (31%), 176 (16%), 166 (100%), 70 (98%).

EXAMPLE III

Figure 3:
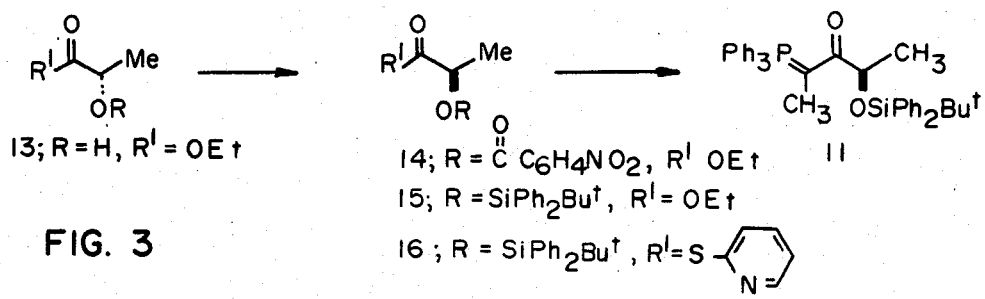
FIG. 3 shows the synthesis of ylide, 11.

Synthesis of Ylide (11) (FIG. 3)

The first step in the synthesis of Ylide 11 employed several steps described below:

(a)

Formation of Ethyl 2-(R)-(4-Nitrobenzoyloxy)propionate (13)

A modification of Mitsunobu's procedure was employed wherein a solution of Ph$_3$P (3.14 g, 12 mmol) and THF was added dropwise at −20° C. to a rapidly stirred solution of diethyl azodicarboxylate (2.0 mL, 12 mmol) and THF (2 mL). A white precipitate appeared within 0.5 h. A solution of 4-nitrobenzoic acid (1.67 g, 10 mmol and THF (15 mL) was added dropwise at −20° C., the resulting mixture was stirred at −20° C. for 0.5 h, and ethyl L-lactate (13) (2.0 mL, 18 mmol, [a]$^{20}$−12 (neat), Aldrich Chemical Co.) was then added by drops. The cooling bath was removed and the reaction mixture was allowed to stir for 27 h. Concentration gave an orange oil which was diluted with ether and filtered to remove a white solid. Purification of the filtrate by chromatography (1:1 hexane-ethyl acetate) gave 2.42 g (91%) of pure 14 as a low melting white solid: mp 42°–43° C. (from hexane), [a]$_D^{25}$−13.1 (c 1.17, EtOH); IR (film) 1720, 1430, 1280, 1110 cm$^{-1}$; $^1$H NMR (250 MHz, CDCl$_3$) 8.2–8.35 (m, aryl H) 5.35 (q, J=7.0 Hz, OCH), 4.25 (q, J=7.1 Hz, OCH$_2$), 1.67 (d, J=7.0 Hz, OCHMe), 1.30 (t, J=7.1 Hz, CH$_2$Me); MS (isobutane CI) m/z 268 (MH), 222, 150, 120, 71; MS (EI) m/z 267.0742 (267.0743 calcd for $C_{12}H_{13}NO_6$).

(b)

Formation of Ethyl 2(R)-(t-butylidiphenylsilyloxy)propanoate (15)

A mixture of 14 (1.66 g, 6.22 mmol), $K_2CO_3$ (850 mg, 6.2 mmol, flame dried) and absolute EtOH (10 mL) was stirred at 23° C. for 15 min. Filtration and concentration of the filtrate gave crude ethyl D-lactate, which was immediately silylated at 23° C. (6 h) in DMF (10 mL) with t-butyldiphenylsilyl chloride (1.8 mL, 7.0 mmol) and imidazole (950 mg, 14 mmol). Aqueous workup (ether, $MgSO_4$) gave a viscous oil which was chromatographed (7:1 hexane-ethyl acetate) to give 1.18 g (53%) of pure 15 as a colorless liquid: $[a]_D^{25}+46.0$ (c 1.97, EtOH), IR (film) 1762, 1110, 1140 cm$^{-1}$; $^1$H NMR (250 MHz, CDCl$_3$) 7.3–7.7 (m, Ph), 4.27 (q, J=6.7 Hz, OCH), 4.02 (q, J=7.1 Hz, OCH$_2$), 1.37 (d, J=6.7 Hz, CHMe, 1.14 (t, J=7.1 Hz, CH$_2$Me), 1.10 (s, t-Bu); MS (EI) m/z 299.1104 (299.1103 calcd for $C_{17}H_{19}SiO_3$, M-Bu, 72%), 227 (70%), 199 (100%).

(c)

Formation of S-2'-Pyridinyl 2-(R)-(t-butyldiphenylsilyloxy)propanthioate (16)

A solution of 15 (775 mg, 2.17 mmol), KOH (620 mg, 8.8 mmol), and MeOH (10 mL) was maintained at 23° C. for 10 h and then concentrated. Acidification with 1N HCl (20 mL), extraction with ether, and drying of the organic extract (MgSO$_4$) provided the corresponding crude acid (579 mg, 82%) as a colorless liquid. This material was immediately esterified in ethyl acetate (10 mL) by reaction with 2-pyridinthiol (222 mg, 2.0 mmol), and dicyclohexylcarbodiimide (474 mg, 2.33 mmol) at 23° C. for 9 h. After separation of the precipitate by filtration, the filtrate was washed with brine, dried (MgSO$_4$) and concentrated to give a yellow oil. Purification on silica gel (4:1 hexane-ethyl acetate) gave 620 mg (68% from 14 of 16 (purity ~90% by $^1$H NMR analysis) as a colorless oil: IR (film) 1715 cm$^{-1}$; $^1$H NMR (250 MHz, CDCl$_3$) 8.6–8.7 (m, C-6 pyridinyl H), 7.2–7.8 (m, pyridinyl H), 4.44 (q, J=6.6 Hz, OCH), 1.26 (d, J=6.6 Hz, CHMe), 1.18 (s, t-Bu); MS (isobutane CI) 422 (MH), 279, 257, 225, 112, 89.

(d)

(Formation of Ylide 2-(R)-(t-butyldiphenylsilyoxy)-4-triphenylphosphoranylidene-3-pentanone (11)

A solution of s-BuLi (1.91 mL of a 1.15M solution in cyclohexane) was added at 23° C. to a rapidly stirred suspension of (ethyl)triphenylphosphonium bromide (816 mg, 2.20 mmol, finely ground and dried in vacuo for 2 d at 200° C.) and THF (15 mL). Over the period of 10 min the white suspension changed to a dark red solution. A solution of 16 (421 mg, 1.00 mmol) and THF (5 mL) was added by drops, the resulting orange suspension was stirred at 23° C. for 20 min, and was then filtered through Celite. Agueous workup (ether, K$_2$CO$_3$) gave 690 mg of a yellow oil. This material was purified by radial chromatography (4 mm silica gel plate, 1:1 hexane-ethyl acetate) to give 323 mg (54%) of ylide 11 as a nearly pure light yellow amorphous solid: IR (film) 1518, 1440, 1110 cm$^{-1}$; $^1$H NMR (250 MHz, CDCl$_3$) 7.3–7.8 (m, Ph), 4.56 (q, J=6.5 Hz, CHO), 1.58 (d, J=6.8 Hz, P=CMe), 1.32 (d, J=6.5 Hz, CHMe), 1.08 (s, t-Bu); MS (CI) m/z 601 (MH), 317, 279, 263, 185, 85.

EXAMPLE IV

Biological Effects of Synthetic Pumiliotoxin B

Synthetic pumiliotoxin B was tested for cardioactive properties on atrial strips prepared from male 250 gm guinea pigs by suspending the strips in 20 ml of a physiologically balanced salt solution aerated with a 95:5 mixture of $O_2:CO_2$ gas as described by Perry in Pharmacological Experiments on Isolated preparations (2nd. Ed., Churchill Livingston, New York, 1970). The effect of synthetic pumiliotoxin B on the rate and force of spontaneous contractions was examined by serial additions of aliquots of the alkaloid in methanol as described by Mensah-Dwumah and Daly in Toxicon, Volume 16, Page 189 (1978). Synthetic pumiliotoxin B increases the force of contractures of spontaneously beating guinea pig atrial strips by 2 to 5 fold with half maximal effects at about 3 uM, and increases rates of atrial contractions by 2–3 fold with half maximal effects at about 6 uM.

We claim:

1. An indolizidine alkaloid with the formula

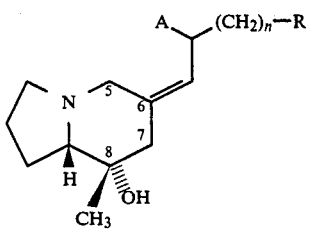

wherein:
(a) A is either CH$_3$ or H, and
(b) n is an integer from 1–9, and
(c) R is CH$_2$OH, CHO, or

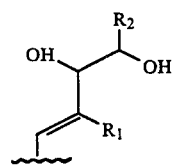

and
(d) R$_1$ and R$_2$ are alkyl groups both larger than CH$_3$, or a combination of alkyl groups, one being CH$_3$ and the other larger than CH$_3$.

2. The indolizidine alkaloid in claim 1 wherein:
(a) A is CH$_3$, n is 1 and R is CH$_2$OH, or
(b) A is CH$_3$, n is 1 and R is CHO, or
(c) A is CH$_3$, n is 1 and R is

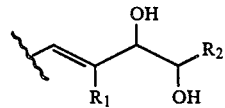

and
(d) R$_1$ and R$_2$ are alkyl groups both larger than CH$_3$, or a combination of alkyl groups, one being CH$_3$ and the other larger than CH$_3$.

3. The indolizidine alkaloid in claim 1 wherein:
(a) A is H, n is 1 and R is CH$_2$OH, or (b) A is H, n is 1 and R is CHO, or
(c) A is H, n is 1 and R is

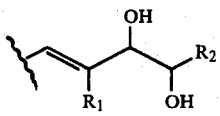

and
(d) $R_1$ and $R_2$ are alkyl groups both larger than $CH_3$, or a combination of alkyl groups, one being $CH_3$ and the other larger than $CH_3$.

4. A method of making indolizidine alkaloid comprising the steps of:
(a) reacting one equivalent of a chiral protected cohydroxy silylalkyne with a hydroaluminating reagent, and less than one equivalent of MeLi in hexane yielding a vinyl alanate, followed by reacting said vinyl alanate with an epoxide yielding a bicyclic carbamate, and
(b) sequential treatment of said bicyclic carbamate with hydroxyl ions effecting hydrolysis of said bicyclic carbamate, and subsequent reaction with formalin and cyclization of the product with camphorsulfonic acid in acetonitrile, and
(c) alcohol protection of the product.

5. The method as defined in claim 4 in which the alcohol protection of the product is oxidized.

6. The method as defined in claim 5 in which said oxidized product is reacted with an ylide and the product reduced.

7. The method as defined in claim 4, wherein:
(a) said chiral protected cohydroxy silylalkyne has the formula

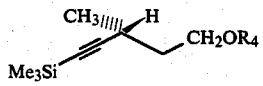

and
(b) said epoxide is the chiral epoxide has the formula

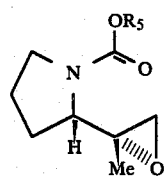

and
(c) said indolizidine alkaloid is the z-alkylideneindolizidine has the formula

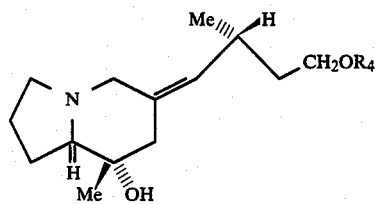

and
(d) $R_4$ and $R_5$ are alcohol protecting groups.

8. A method as defined in claim 4 in which:
(a) said chiral protected cohydroxy silylalkyne has the formula

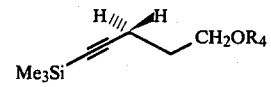

and
(b) said epoxile is the chiral epoxide has the formula

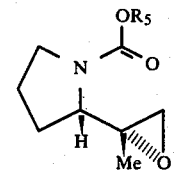

and
(c) said indolizidine alkaloid is the z-alkylideneindolizidine has the formula

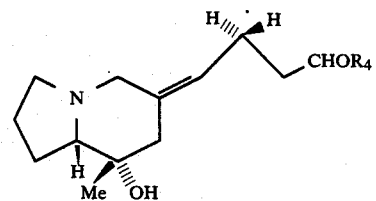

and
(d) $R_4$ and $R_5$ are alcohol protecting groups.

9. The method as defined in claim 6 in which said ylide has the formula:
(a)

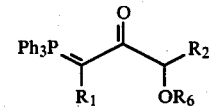

and
(b) $R_1$ and $R_2$ are $CH_3$ or $CH_3CH_2$ and $R_6$ is an alcohol protecting group.

10. A method for increasing the force and rate of atrial tissue contractions comprising contacting indolizidine alkaloids with said atrial tissue in aqueous solution containing 3-6 uM of said indolizidine alkaloids wherein said indolizidine alkaloids have the structure

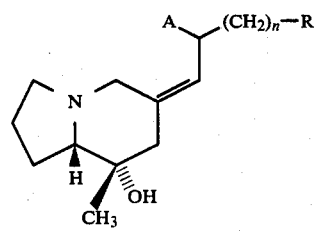

and;
(a) A is either $CH_3$ or H, and
(b) n is an integer from 1-9, and
(c) R is $CH_2OH$, CHO, or

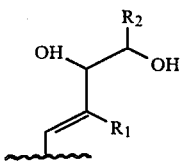

and (d) R₁ and R₂ are alkyl groups both larger than CH₃, or a combination of alkyl groups, one being CH₃ and the other larger than CH₃.

11. A method for increasing the force and rate of atrial tissue contractions comprising contacting indolizidine alkaloids with said atrial tissue in aqueous solution containing 3-6 uM of said indolizidine alkaloids wherein said indolizidine alkaloids have the structure

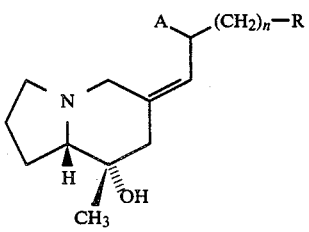

and (a) A is CH₃, n is 1 and R is CH₂OH or
(b) A is CH₃, n is 1 and R is CHO, or
(c) A is CH₃, n is 1 and R is

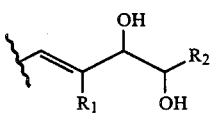

and (d) R₁ and R₂ are alkyl groups larger than CH₃, or a combination of alkyl groups, one being CH₃ and the other larger than CH₃.

12. A method for increasing the force and rate of atrial tissue contractions comprising contacting said indolizidine alkaloids with said atrial tissue in aqueous solution containing 3-6 uM of said indolizidine alkaloids wherein said indolizidine alkaloids have the structure

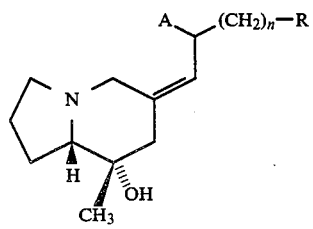

and (a) A is H, n is 1 and R is CH₂OH, or
(b) A is H, n is 1 and R is CHO, or
(c) A is H, n is 1 and R is

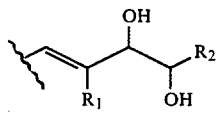

and (d) R₁ and R₂ are alkyl groups larger than CH₃, or a combination of alkyl groups, one being CH₃ and the other larger than CH₃.

13. A method of synthesizing indolizidine alkaloid comprising the steps of:

(a) reacting one equivalent of a chiral protected silylalkyne at about room temperature with one equivalent of a hydroaluminating reagent and with about 0.85 equivalent of MeLi in hexane yielding a vinyl alanate;

(b) reacting at about 60° C. said vinyl alanate with about 0.44 equivalents of an epoxide having the structure

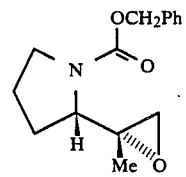

yielding a bicyclic carbamate having the structure

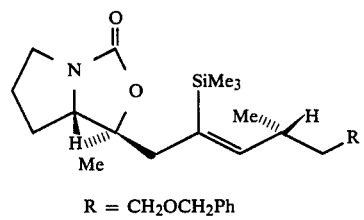

R = CH₂OCH₂Ph (c) sequentially treating said bicyclic carbamate with hydroxyl ions at about 90° C. to effect hydrolysis of said bicyclic carbamate, to give an intermediate that upon nitrogen deprotection is cyclizable yielding a Z-6-alkylideneindolizidine.

14. A method as defined in claim 13 in which the protected product is oxidized.

15. A method as defined in claim 14 in which said oxydized product is reacted with a ylide comprising the structure

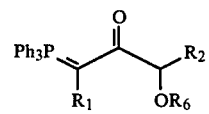

where R₁ and R₂ are CH₃ and R₆ is an alcohol protecting group.

16. A method for increasing the force and rate of atrial tissue contractions comprising contacting substantially pure synthetic indolizidine alkaloids with said atrial tissue in aqueous solution containing 3-6 uM of said indolizidine alkaloids wherein said indolizidine alkaloids have the structure

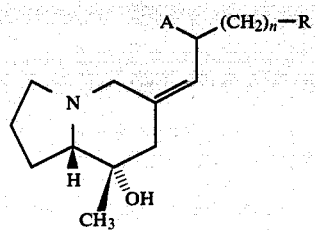

and;
(a) A is either CH₃ or H, and
(b) n is an integer from 1-9, and
(c) R is CH₂OH, CHO, or

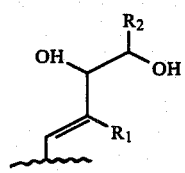

and
(d) R₁ and R₂ are alkyl groups both larger than CH₃, or a combination of alkyl groups, one being CH₃ and the other larger than CH₃.

17. A method for increasing the force and rate of atrial tissue contractions comprising contacting substantially pure synthetic indolizidine alkaloids with said atrial tissue in aqueous solution containing 3-6 uM of said indolizidine alkaloids wherein said indolizidine alkaloids have the structure

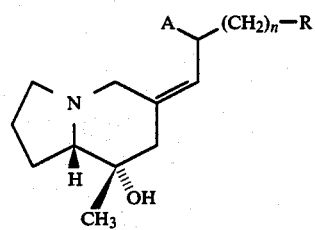

and
(a) A is CH₃, n is 1 and R is CH₂OH, or
(b) A is CH₃, n is 1 and R is CHO, or
(c) A is CH₃, n is 1 and R is

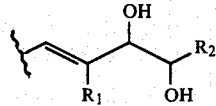

(d) R₁ and R₂ are alkyl groups both larger than CH₃, or a combination of alkyl groups, one being CH₃ and the other larger than CH₃.

18. A method for increasing the force and rate of atrial tissue contractions comprising contacting substantially pure synthetic indolizidine alkaloids with said atrial tissue in aqueous solution containing 3-6 uM of said indolizidine alkaloids wherein said indolizidine alkaloids have the structure

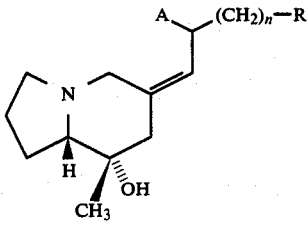

and
(a) A is H, n is 1 and R is CH₂OH, or
(b) A is H, n is 1 and R is CHO, or
(c) A is H, n is 1 and R is

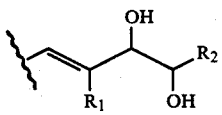

and
(d) R₁ and R₂ are alkyl groups both larger than CH₃, or a combination of alkyl groups, one being CH₃ and the other larger than CH₃.

* * * * *